United States Patent [19]

Harris et al.

[11] 4,082,806

[45] Apr. 4, 1978

[54] PREPARATION OF TETRAKETONES

[75] Inventors: Frank W. Harris, Xenia; Bruce A. Reinhardt, Dayton, both of Ohio

[73] Assignee: Wright State University, Dayton, Ohio

[21] Appl. No.: 641,958

[22] Filed: Dec. 18, 1975

[51] Int. Cl.$^2$ .............................................. C07C 49/76
[52] U.S. Cl. ............................ 260/590 D; 260/297 R
[58] Field of Search ............... 260/590 D, 590 R, 591, 260/297 R

[56] References Cited

U.S. PATENT DOCUMENTS 3,839,497   8/1974   Wentworth ..................... 260/590 D

OTHER PUBLICATIONS

Fieser et al., Reagents for Organic Synthesis, pp. 161-162, 303-304.

Primary Examiner—James O. Thomas, Jr.
Assistant Examiner—James H. Reamer
Attorney, Agent, or Firm—Biebel, French & Nauman

[57] ABSTRACT

A method of preparing tetraketone precursors which are useful in the production of high temperature resistant polyquinoxaline resins. Suitable diketones are oxidized with a halogenating agent, such as cupric halide or hydrogen bromide, and dimethylsulfoxide to produce the corresponding tetraketone. The tetraketones which can be produced by the instant process have the formula:

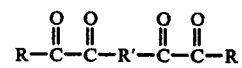

wherein R is hydrogen or an aryl, substituted aryl, heterocyclic or substituted heterocyclic radical and R' is an aryl, substituted aryl, arylalkyl, arylether, arylthioether, arylsulfoxide, arylsulfone, heterocyclic or substituted heterocyclic radical.

10 Claims, No Drawings

PREPARATION OF TETRAKETONES

CROSS-REFERENCE TO RELATED APPLICATIONS

Reference is made to applicants' copending application Ser. No. 641,959 now U.S. Pat. No. 4,046,814, filed on even date herewith and assigned to the same assignee.

BACKGROUND OF THE INVENTION

The present invention relates to a method for producing tetraketones of a type which are themselves useful in the production of thermally stable quinoxaline polymers.

Polyquinoxaline resins have become widely sought after in recent years due to their unique thermal properties. Because of their desirable properties, the polymers are useful for high temperature adhesives, coatings and films in a number of critical industries. As stated in Stille, U.S. Pat. No. 3,661,850, polyquinoxaline polymers are "suitable for high temperature electrical insulators, battery separators, foams, ablative materials for re-entry bodies and rocket nozzles". Other patents which discuss these unique resins, their properties, and uses are: Augl, U.S. Pat. Nos. 3,766,141 and 3,642,700; and Hergenrother, U.S. Pat. No. 3,778,412.

Stille, Augl and Hergenrother all disclose methods of preparing polyquinoxalines from tetraketones of the following general formula:

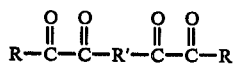

In Stille R is said to be selected from the group consisting of alkyl, aryl, alkaryl, and aralkyl groups and hydrogen, while R' is selected from the group consisting of alkylene, arylene, aralkylene and alkarylene groups (Col. 3, lines 6–16). Similarly in Augl, R is listed as $C_6H_5$ or H and R' is m-phenylene, p-phenylene or a number of diphenyl compounds (Col. 2, lines 29–64 of U.S. Pat. No. 3,766,141). In Hergenrother, R is stated to be hydrogen, alkyl, phenyl and substituted phenyl and R' is for the most part selected from a number of divalent alkyl, phenyl and diphenyl compounds (Col. 3, lines 1–34).

These prior art patents also list several methods of preparing the desired tetraketone precursors used in the manufacture of the polyquinoxaline resins. Included are the methods described in *Helv. Chim. Acta.*, 27, 496 (1939), *Helv. Chim. Acta.*, 24 899 (1941) and *Bull. Soc. Chim. France*, 636 (1956) (Stille, Col. 5, lines 9–24), and those in Hergenrother and Augl, (Hergenrother, Examples 3–5; Augl, Col. 3, lines 3–36), all of which disclose methods wherein diketones are oxidized to tetraketones with selenium dioxide or selenious acid. These reagents, however, are reduced during the reaction to selenium metal which is highly toxic and extremely difficult to remove from the reaction mixture. The reagents are also expensive.

As noted in Wentworth, U.S. Pat. No. 3,839,497, expense in preparation of the tetraketone precursor has resulted in current high costs for the polyquinoxaline resins. Accordingly, Wentworth suggests an alternative method for producing 1,4-bis(phenylglyoxaloyl) benzene. That method involves reacting cuprous phenylacetylide and p-diiodobenzene to form p-bis(phenylethynyl) benzene which is then placed in a reaction chamber with N-bromosuccinimide and a dimethylsulfoxide solvent and oxidizing agent. A p-bis(phenyl glyoxaloyl) benzene precipitate is formed.

While this method is a possibility, is still does not appear to offer a feasible way of obtaining large quantities of tetraketones rapidly and inexpensively.

Thus, the production of tetraketones by the prior art processes has been limited. Therefore, the need exists for an improved process for producing large quantities of tetraketones as inexpensively as possible.

SUMMARY OF THE INVENTION

In accordance with the present invention, there is provided a method for economically producing large amounts of tetraketones of the type:

where R is hydrogen, an aryl radical, a substituted aryl radical, such as alkylaryl, haloaryl, cyanoaryl, nitroaryl, alkoxyaryl, etc., a heterocyclic radical, or a substituted heterocyclic radical, and R' is an aryl radical, a substituted aryl radical, an arylalkyl radical, such as diphenylmethyl, diphenylethyl, etc, an arylether radical; an arylthioether radical, and arylsulfoxide radical, an arylsulfone radical, a heterocyclic radical, or a substituted heterocyclic radical.

The instant method for preparing tetraketones of this type involves the oxidation of diketones with a halogenating agent and dimethylsulfoxide. Diketones of either of the following two formulas may be used:

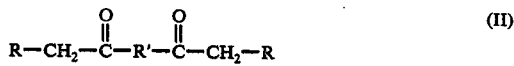

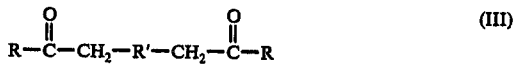

In each instance R and R' are the same as in Formula (I). Most of the diketones of Formula (II) are preferably prepared in the manner described in our copending application Ser. No. 641,959 now U.S. Pat. No. 4,046,814, filed on even date herewith. Others, including the diketones of Formula (III) may be prepared by Friedel-Crafts reactions of the type described in Augl or Hergenrother.

Diketones of Formulas (II) and (III) can be oxidized with a mixture of a halogenating agent such as cupric halide, i.e., cupric bromide or cupric chloride, and dimethylsulfoxide to afford the corresponding tetraketones of Formula (I) in high yields. The reaction also produces a high yield of cuprous halide, i.e., cuprous bromide or cuprous chloride. At present day prices, this by-product is approximately four times as expensive as the cupric halide starting material. Commerical exploitation of the by-product, thus, makes the method of the instant invention economically attractive indeed as a means of providing tetraketone precursors. Other halogenating agents such as hydrogen bromide may be used in place of the cupric halide.

With such a ready supply of inexpensive tetraketones, the sought after high temperature resistant polyquinoxaline resins mentioned in the Background of the Invention can be prepared by the processes of Stille, Augl or Hergenrother at a greatly reduced cost.

Accordingly, it is an object of the present invention to provide an inexpensive means to produce large quantities of tetraketone precursors for use in manufacturing thermally stable polyquinoxaline resins.

Another object of the invention is to provide a method of oxidizing diketones to tetraketones using cupric halides and dimethylsulfoxide with the concomitant yielding of a valuable cuprous halide by-product.

Other objects and advantages of the invention will be apparent from the following description of the accompanying claims.

DESCRIPTION OF THE PREFERRED EMBODIMENTS

The oxidation reaction of the present invention can be carried out in one or two steps. In the one step process, the diketone, halogenating agent and dimethylsulfoxide are mixed and reacted for a sufficient period of time to yield tetraketone. The oxidation reaction can be run with or without a solvent present, but preferably the operation is carried out in an inert solvent. Any liquid solvent that is inert under the reaction conditions can be used. Examples are: esters; ethers; aliphatic, cycloaliphatic or aromatic hydrocarbons or chlorinated hydrocarbons; etc. Mixtures of these solvents can also be used.

The diketone, halogenating agent, and dimethylsulfoxide can be premixed or mixed in situ. Preferably, the diketone, the halogenating agent, and the dimethylsulfoxide are mixed in an inert liquid solvent at a temperature of from about 0° C to about 150° C. The reaction time can vary from one hour to forty-eight hours. The selection of the solvent or solvents, the temperature and the reaction time will depend on the particular diketone used.

In the two step procedure, the first step involves the use of a halogenating agent to give a di(alpha-haloketone) of the type:

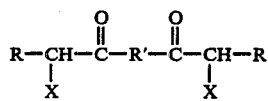  (IV)

or the type:

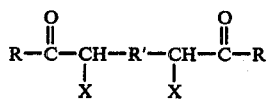  (V)

wherein R and R' are the same as those given for Formulas I-III and X is bromine or chlorine.

The reaction is carried out in an inert solvent at a temperature of from about 0° C to about 150° C. Any solvent that is inert under the reaction conditions can be used. Included are the solvents previously mentioned in regard to the one-step procedure. The reaction is run for a time sufficient to effect substantial conversion of the diketone to the halogenated form of Formulas IV or V. Again, the reaction time can vary considerably, for example, from one hour to twenty-four hours.

The di(alpha-haloketone) is then isolated by evaporating the solvent. It is converted to the corresponding tetraketone by use of dimethylsulfoxide. This second step in the reaction may be carried out with or without an inert solvent of the type mentioned. Preferably the di(alphahaloketone) is treated with a large excess of dimethylsulfoxide, which also functions as the solvent, at a temperature of from about 0° C to about 190° C. The reaction time may vary from 1 to 48 hours.

Rather than evaporating off the solvent from the first step, alternatively the di(alpha-haloketone) can be oxidized in situ in the second step by adding dimethylsulfoxide to the reaction mixture and stirring at a temperature of from about 0° C to about 190° C for a period of 1 to 48 hours. As was the case with the preferred one-step procedure, the choice of solvent, temperature and time are dependent upon the particular diketone starting material.

Any diketone of the type previously described (Formulas II and III) can be converted to the corresponding tetraketone (Formula I) by the process of this invention. Exemplary compounds are: 1,4-bis(phenylacetyl)benzene, 4,4'-bis(phenylacetyl)diphenyl ether, 1,3-diphenacylbenzene, 4,4'-bis(phenylacetyl)diphenylmethane, 2,6-diphenacylbenzene, 1,3-bis(2-pyridylacetyl)benzene, 4,4'-bis(phenylacetyl)di-phenylsulfoxide, 1,3-bis(4-methylphenylacetyl)benzene, 1,4-bis(5-fluoro-2-nitrophenylacetyl)benzene, and α,α'-dibenzoylparaxylene.

Also as mentioned previously, certain diketones of this type can be prepared in accordance with our copending application Ser. No. 641,959 now U.S. Pat. No. 4,046,814, which is herein incorporated by reference. Basically, that process involves the reaction of dicarboxylic acid derivatives that contain no alpha hydrogens (i.e., aromatic diesters, substituted aromatic diesters, heterocyclic diesters, aromatic diacylhalides, etc.) with active-hydrogen compounds of the type:

where R is an aryl radical, a substituted aryl radical, a heterocyclic radical, or a substituted heterocyclic radical, and X is a nitrile group or a carboxylic acid functional group, such as a carboxylic ester, a carboxylic amide, etc. The reaction is carried out in the presence of a strong base such as sodium hydride, sodium amide, sodium triphenylmethyl, etc. An intermediate having the formula

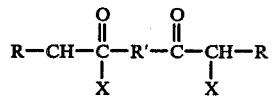

wherein R and R' are aryl, substituted aryl, heterocyclic or substituted heterocyclic and X is a nitrile or carboxylic acid functional group, is formed. The intermediate is hydrolyzed and decarboxylated to form the diketone.

Other methods may also be used to prepare the diketone starting material. For example, certain diketones falling within the scope of Formulas II and III can be obtained via the reaction of the appropriate dinitrile with Grignard reagents. Likewise, Augl in U.S. Pat. No. 3,766,141 discloses a reaction in which certain other diketones are prepared by reacting dicarboxylic acid derivatives under standard conditions with thionyl chloride to form the acid chloride compound. The acid chloride compound is then reacted wtih benzene and aluminum chloride under typical Friedel-Crafts conditions to obtain a phenylacetyl compound (Col. 3, lines 3-36).

See also, Hergenrother (U.S. Pat. No. 3,778,412) which suggests preparation of p,p'-diacetyldiphenyl ether by Friedel-Crafts acetylation of diphenyl ether in methylene chloride (Example 3); preparation of p,p'-di(phenylacetylphenyl) ether by mixing diphenyl ether and phenylacetyl chloride in methylene chloride, adding that mixture to a suspension of anhydrous aluminum chloride in methylene chloride under nitrogen, and separating and recrystallizing (Example 4); and preparing p-di(phenacyl) benzene from a benzene solution of the diacid chloride of p-phenylenediacetic acid which was added to a slurry of anhydrous aluminum chloride (Example 5).

No matter how prepared, diketones of Formulas II and III are suitable as the starting material in the process of this invention. The following examples will illustrate the process of preparing tetraketones in accordance with this invention.

EXAMPLE 1

This example illustrates the preparation of 1,4-bis(phenylglyoxalyl) benzene from 1,4-bis(phenylacetyl) benzene. A mixture of 0.022 mole of 1,4-bis(phenylacetyl) benzene, 0.073 mole cupric bromide, and 0.210 mole dimethylsulfoxide in 35 ml. of ethyl acetate was heated at 85° C for 20 hours. The ethyl acetate was then removed under reduced pressure and the residue added to 600 ml. of water. The precipitate that formed, which consisted of tetraketone and cuprous bromide, was collected by filtration. The solid mixture was the stirred in 250 ml. of hot ethyl acetate to dissolve the tetraketone. The solution was filtered to yield 0.065 mole of pure cuprous bromide. The filtrate was evaporated under reduced pressure to afford 0.020 mole of pure 1,4-bis(phenylglyoxalyl)benzene.

EXAMPLE 2

This example illustrates the preparation of 4,4'-bis (phenylglyoxalyl)diphenylether from 4,4'-bis(phenylacetyl)diphenyl ether. A mixture of 0.030 mole of 4,4'-bis(phenylacetyl) diphenyl ether and 0.100 mole of cupric bromide in 50 ml. of a 1:1 mixture of chloroform and ethylacetate was heated at reflux for 3 hours. The reaction mixture was cooled, and the precipitate that formed was collected by filtration to afford 0.090 mole of pure cuprous bromide. The filtrate was treated with charcoal, filtered, and evaporated under reduced pressure. Dimethylsulfoxide (0.350 mole) was added to the residue, and the solution was heated at 50° C for 18 hours. The dimethylsulfoxide was then removed under reduced pressure. The oily residue was dissolved in 25 ml. of chloroform and chromatographed on acid-washed alumina to afford 0.024 mole of pure 4,4'-bis(phenylglyoxalyl) ether.

EXAMPLE 3

This example illustrates the preparation of 1,4-bis (phenylglyoxalyl) benzene. A mixture of 0.022 mole of 1,4-bis (phenylacetyl) benzene and 0.210 mole dimethylsulfoxide in 35 ml. ethylacetate was stirred at room temperature with the constant addition of anhydrous HBr gas until a yellow color persisted. The reaction mixture was allowed to stir at room temperature for 18 hours. The ethylacetate was removed under reduced pressure and the resulting yellow solid collected and washed with absolute ethanol. The crude material was recrystallized from absolute ethanol to yield 0.018 mole of pure 1,4-bis)phenylglyoxalyl) benzene.

EXAMPLE 4

This example illustrates the preparation of 2,6-bis (phenylglyoxalyl) pyridine. A mixture of 0.011 mole of 2,6-diphenacylpyridine, 0.036 mole cupric bromide, and 0.105 mole dimethylsulfoxide in 20 ml. of ethylacetate was refluxed for 18 hours. The ethylacetate was removed under reduced pressure and the residue added to 600 ml. of water. The solid was filtered, air dried, and stirred with a 15% solution of ammonium hydroxide. The product was filtered, washed with water, and again air dried. The resulting crude solid was dissolved in 20 ml. of chloroform and chromatographed on a dry column of silica gel to afford 0.006 mole of pure 2,6-bis(phenylglyoxalyl)pyridine.

While the methods herein described constitute preferred embodiments of the invention, it is to be understood that the invention is not limited to these precise methods, and that changes may be made therein without departing from the scope of the invention which is defined in the appended claims.

What is claimed is:

1. The method of preparing a tetraketone having the formula

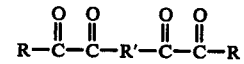

wherein R' is selected from the group consisting of phenyl, diphenyl ether, diphenyl methane, pyridine, diphenyl sulfoxide, and xylene radicals and R is selected from the group consisting of phenyl, substituted phenyl, and pyridyl radicals from a diketone selected from the group consisting of 1,4-bis (phenylacetyl) benzene, 4,4'-bis(phenylacetyl) diphenyl ether, 1,3-diphenacylbenzene, 4,4'-bis(phenylacetyl)diphenylmethane, 2,6-diphenacylpyridine, 1,3-bis(2-pyridylacetyl) benzene, 4,4'-bis(phenylacetyl)diphenylsulfoxide, 1,3-bis(4-methylphenylacetyl)benzene, 1,4-bis(5-fluoro-2-nitrophenylacetyl)benzene, and α,α'-dibenzoyl-para-xylene, comprising oxidizing said diketone to said tetraketone with dimethylsulfoxide and a halogenating agent selected from the group consisting of cupric halide and hydrogen bromide.

2. The method of claim 1 wherein an inert solvent is employed.

3. The method of claim 2 wherein said diketone is first contacted with a halogenating agent selected from the group consisting of cupric halide and hydrogen bromide in the presence of said inert solvent and reacted at 0° C to 150° C for between 1 and 24 hours to form a di(alpha-haloketone) reaction produce which is then treated with said dimethylsulfoxide at 0° C to 190° C for between 1 and 48 hours to form said tetraketone.

4. The method of claim 3 wherein said di(alphahaloketone) reaction product is isolated from said solvent prior to treatment with said dimethylsulfoxide.

5. The method of claim 3 wherein said halogenating agent is cupric bromide.

6. The method of claim 1 wherein a halogentating agent selected from the group consisting of cupric halide and hydrogen bromide and said dimethylsulfoxide are mixed together with said diketone and reacted at 0° to 150° C for between 1 and 48 hours to form said tetraketone.

7. The method of claim 1 wherein said diketone is 1,4-bis(phenylacetyl) benzene.

8. The method of claim 1 wherein said diketone is 4,4'-bis(phenylacetyl) diphenyl ether.

9. The method of claim 1 wherein said halogenating agent is cupric halide and cuprous halide is recovered as a by-product.

10. The method of claim 9 wherein said cupric halide is cupric bromide.

* * * * *